US012758265B2

(12) United States Patent
Yoo et al.

(10) Patent No.: US 12,758,265 B2
(45) Date of Patent: Oct. 13, 2026

(54) BONE GROWTH STIMULATOR

(71) Applicant: M.D.ON BIO CO., LTD., Busan (KR)

(72) Inventors: Seung Jin Yoo, Busan (KR); Hee Seok Yoon, Busan (KR)

(73) Assignee: M.D.ON BIO CO., LTD., Busan (KR)

( * ) Notice: Subject to any disclaimer, the term of this patent is extended or adjusted under 35 U.S.C. 154(b) by 427 days.

(21) Appl. No.: 18/199,635

(22) Filed: May 19, 2023

(65) Prior Publication Data

US 2024/0307094 A1 Sep. 19, 2024

(30) Foreign Application Priority Data

Mar. 14, 2023 (KR) ........................ 10-2023-0033104

(51) Int. Cl.
*A61B 17/66* (2006.01)
*A61B 17/64* (2006.01)

(52) U.S. Cl.
CPC .......... *A61B 17/66* (2013.01); *A61B 17/6441* (2013.01)

(58) Field of Classification Search
CPC .............................................. A61B 17/60–666
See application file for complete search history.

(56) References Cited

U.S. PATENT DOCUMENTS

| | | | | | |
|---|---|---|---|---|---|
| 4,220,146 | A * | 9/1980 | Cloutier | A61B 17/6425 | 606/90 |
| 4,968,316 | A * | 11/1990 | Hergenroeder | A61B 17/6425 | 606/57 |
| 4,988,349 | A * | 1/1991 | Pennig | A61B 17/66 | 606/57 |
| 5,803,924 | A * | 9/1998 | Oni | A61B 17/6416 | 606/57 |
| 5,976,125 | A * | 11/1999 | Graham | A61B 17/6425 | 606/32 |
| 6,162,223 | A * | 12/2000 | Orsak | A61B 17/6425 | 606/59 |
| 6,537,274 | B1 * | 3/2003 | Katz | A61B 17/8685 | 606/56 |
| 7,507,240 | B2 * | 3/2009 | Olsen | A61B 17/6475 | 606/57 |

(Continued)

FOREIGN PATENT DOCUMENTS

| | | | |
|---|---|---|---|
| KR | 10-1666527 | B1 | 10/2016 |
| KR | 10-1803423 | B1 | 11/2017 |

*Primary Examiner* — Eduardo C Robert
*Assistant Examiner* — Steven J Cotroneo
(74) *Attorney, Agent, or Firm* — Bridgeway IP Law Group, PLLC; Sang Ho Lee; Hyun Woo Shin

(57) ABSTRACT

A bone growth stimulator includes a first screw fastened to the metaphysis portion and having a channel penetrating between a front end and a rear end, a second screw fastened to the metaphysis portion while being disposed in parallel to the first screw and having a channel penetrating between a front end and a rear end, a first rod pin having one side passing through a human tissue that surrounds the long bone and being inserted into the channel of the first screw, and another side exposed to the outside of the human tissue, a second rod pin having one side passing through a human tissue that surrounds the long bone and being inserted into the channel of the second screw, and another side exposed to the outside of the human tissue, and a pressing unit for applying a force in a direction for spacing the first rod pin apart from the second rod pin.

18 Claims, 7 Drawing Sheets

(56) References Cited

U.S. PATENT DOCUMENTS

| | | | | |
|---|---|---|---|---|
| 7,763,020 | B2 * | 7/2010 | Draper | A61B 17/6425 606/59 |
| 9,492,199 | B2 * | 11/2016 | Orsak | A61B 17/6466 |
| 2003/0120273 | A1 * | 6/2003 | Cole | A61B 17/66 606/57 |
| 2005/0203509 | A1 * | 9/2005 | Chinnaian | A61B 17/6491 606/54 |
| 2010/0125273 | A1 * | 5/2010 | Schwieger | A61B 17/686 606/59 |
| 2012/0143191 | A1 * | 6/2012 | Foote | A61B 17/6425 606/59 |
| 2014/0025075 | A1 * | 1/2014 | Hokanson | A61B 17/66 606/58 |

* cited by examiner

BONE GROWTH STIMULATOR

CROSS-REFERENCE TO RELATED APPLICATION

This application claims priority to Korean patent application No. 10-2023-0033104, filed on Mar. 14, 2023, the entire disclosure of which is incorporated herein by reference.

TECHNICAL FIELD

The present invention relates to bone growth stimulators, and more particularly, to a bone growth stimulator with an improved structure that enables growth promotion of a growth plate and suppresses damage or breakage of a long bone due to sudden application of a large tensile force to a screw implanted in the long bone to promote the growth plate.

BACKGROUND ART

In general, long bones such as the femur, tibia, and humerus include a diaphysis forming a central portion, a metaphysis provided at both ends of the diaphysis, and an epiphysis provided on an outer portion of the metaphysis, and a growth plate is located between the metaphysis and the epiphysis. In this case, an intramedullary cavity filled with bone marrow may exist inside the diaphysis, and bones may grow through the growth plate.

It is known that a length growth of the growth plate of the long bones is inhibited when an inward compressive force from the epiphysis toward the metaphysis is applied to the growth plate, and the length growth of the growth plate of the long bones is promoted when an outward tensile force from the metaphysis toward the epiphysis is applied to the growth plate.

Accordingly, in the conventional art, a device for promoting bone growth by implanting a screw in bones located above and below the growth plate and applying a tensile force to one side of the screw exposed to the outside has been devised.

However, according to such a conventional bone growth stimulator, when a tensile force is applied to a portion of a screw exposed to the outside to promote bone growth, the tensile force is transmitted to the bones through a main body of the screw implanted in the bones without changes, and, thus, as an excessively large force is applied to a contact area between both ends of a bone penetration area and the screw due to a reason such as a procedure by a person other than a skilled doctor or carelessness, cracks or damage has frequently occurred in the contact area or even the bones into which the screw has been implanted has been frequently damaged.

DESCRIPTION OF EMBODIMENTS

Technical Problem

Provided is a bone growth stimulator that enables growth promotion of a growth plate and suppresses damage or breakage of a long bone due to an external force for promoting the growth plate.

Solution to Problem

According to an embodiment of the present invention, a bone growth stimulator promotes growth of a long bone by applying a tensile force to a growth plate existing between a metaphysis portion and an epiphysis portion forming the long bone, and includes a first screw fastened to the metaphysis portion and having a channel penetrating between a front end and a rear end, a second screw fastened to the metaphysis portion while being disposed in parallel to the first screw and having a channel penetrating between a front end and a rear end, a first rod pin having one side passing through a human tissue that surrounds the long bone and being inserted into the channel of the first screw, and another side exposed to the outside of the human tissue, a second rod pin having one side passing through a human tissue that surrounds the long bone and being inserted into the channel of the second screw, and another side exposed to the outside of the human tissue, and a pressing unit for applying a force in a direction for spacing the first rod pin apart from the second rod pin.

The pressing unit may include a guide body in which a transfer screw is rotatably installed on an inner side and a rotation knob dynamically connected to the transfer screw is rotatably installed on an outer side, a fixing member fixed to the guide body and on which the second rod pin is selectively mounted, and a movable member movably installed on the guide body and including a nut portion screw-coupled to the transfer screw and a seating portion on which the first rod pin is selectively mounted.

The bone growth stimulator may further include a torque wrench dynamically connected to the rotation knob such that only a torque of less than a set value is applied to the rotation knob.

The pressing unit may include a first connection member having a through hole through which the first rod pin passes, and connected to the first rod pin through the through hole, a second connection member having a through hole through which the second rod pin passes, and connected to the second rod pin through the through hole, and an elastic member interposed between the first connection member and the second connection member to apply a force in a direction for spacing the first connection member apart from the second connection member.

The pressing unit may include an elastic member interposed between the first rod pin and the second rod pin in a coiled form to apply an elastic force to each of the first and second rod pins.

Effects of Disclosure

A bone growth stimulator according to the present invention having such a configuration as described above implants a first screw and a second screw in a long bone with a growth plate interposed therebetween, inserts a first rod pin and a second rod pin, which are thinner and longer than the first and second screws, into respective channels of the first and second screws so that respective both ends of the first and second rod pins are exposed to the outside, and applies a force to the exposed both ends by using a pressing unit such that the first rod pin is spaced apart from the second rod pin, so that, even when a force greater than an optimum value required to elongate a growth plate is applied to each of the first and second rod pins, the applied force gradually decreases from the exposed end of the rod pin to a portion of the rod pin in contact with the screw implanted in the bone due to the bending characteristics of the rod pin formed to be thinner and longer than the screw and the characteristics that the rod pin restores to its original shape after being bent. Thus, a large force is prevented from being suddenly transmitted to bones through the screw implanted in the bone, and consequently, damage or breakage of the bone during a procedure for elongating the growth plate may be suppressed, and growth of the growth plate may be promoted.

DETAILED DESCRIPTION

Figure 1:
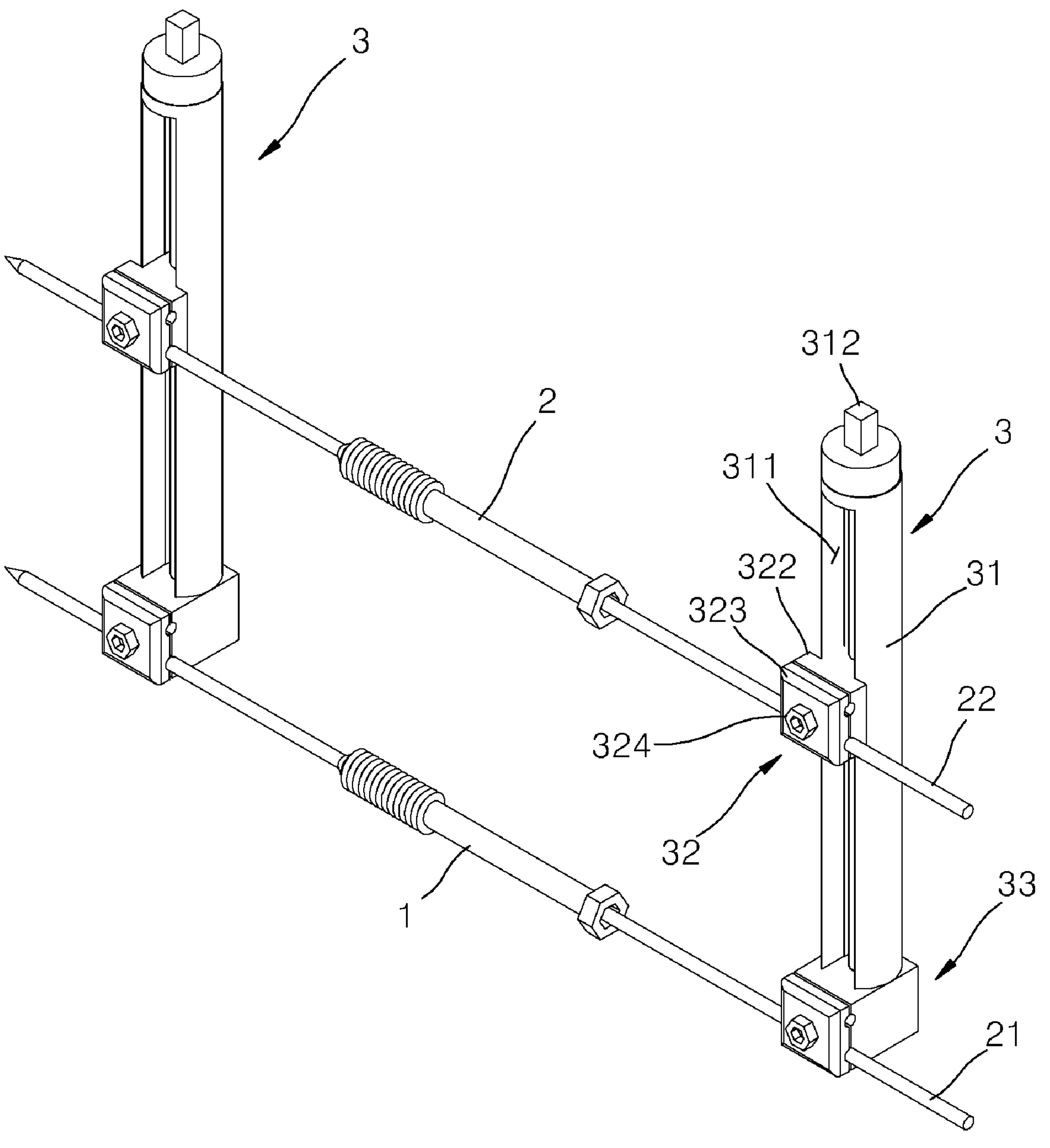
FIG. 1 is a perspective view of a bone growth stimulator according to an embodiment of the present disclosure.

In the following description, in order to clarify the understanding of the present invention, descriptions of well-known technologies for the features of the present invention will be omitted. The following embodiment are detailed descriptions to help the understanding of the present invention, and it will be understood that the scope of the present invention is not limited. Accordingly, an equivalent invention that performs the same function as the present invention will also fall within the scope of the present invention.

In addition, in the following description, the same reference numerals or symbols means the same configuration, and unnecessary redundant description and description of known technology will be omitted. Moreover, a description of each embodiment of the present invention that overlaps with the description of the technology that is the background of the present invention will also be omitted.

A bone growth stimulator according to an embodiment of the present invention will now be described in detail with reference to the accompanying drawings.

Figure 2:
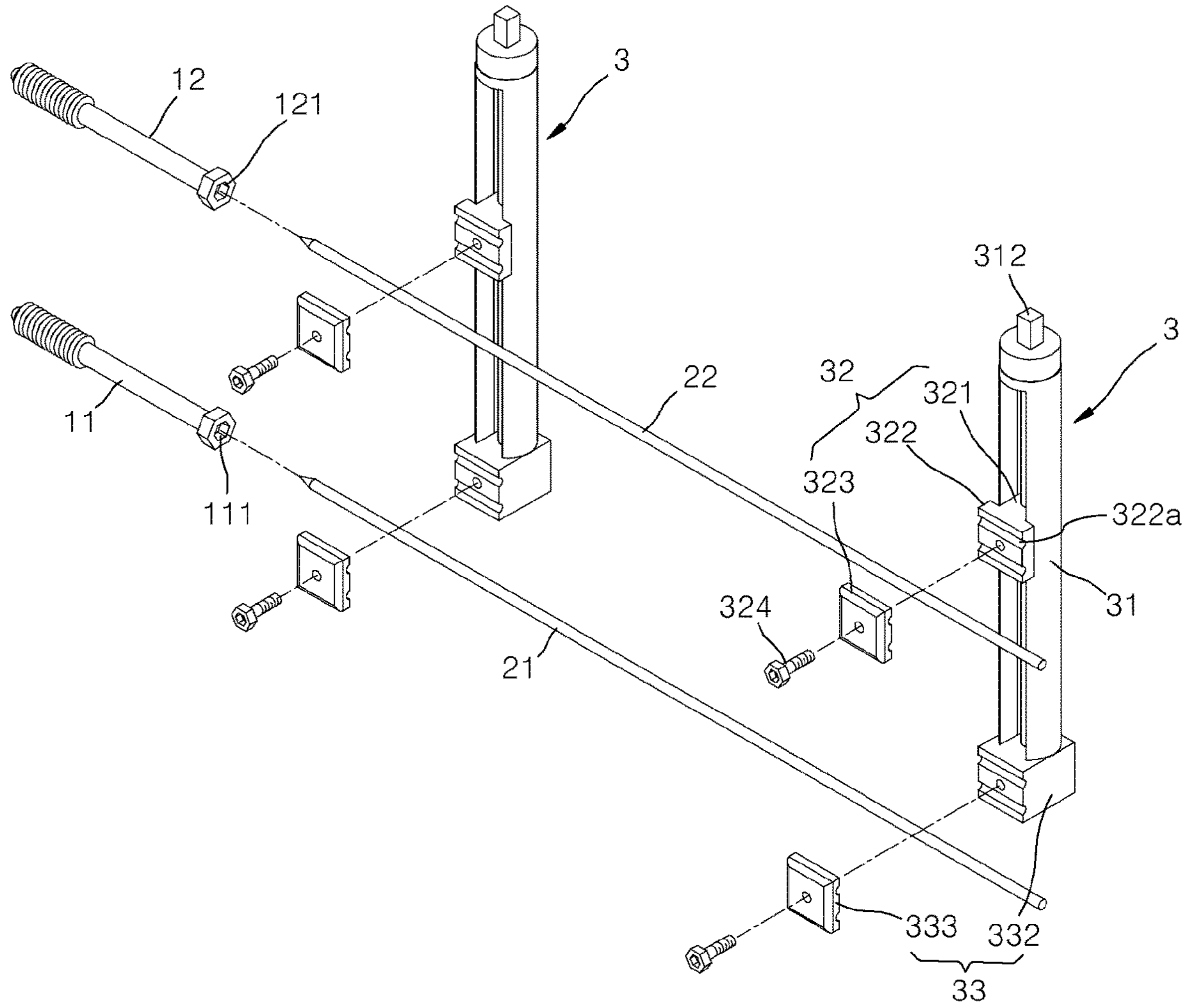
FIG. 2 is an exploded perspective view of an embodiment of the present disclosure.
Figure 3:
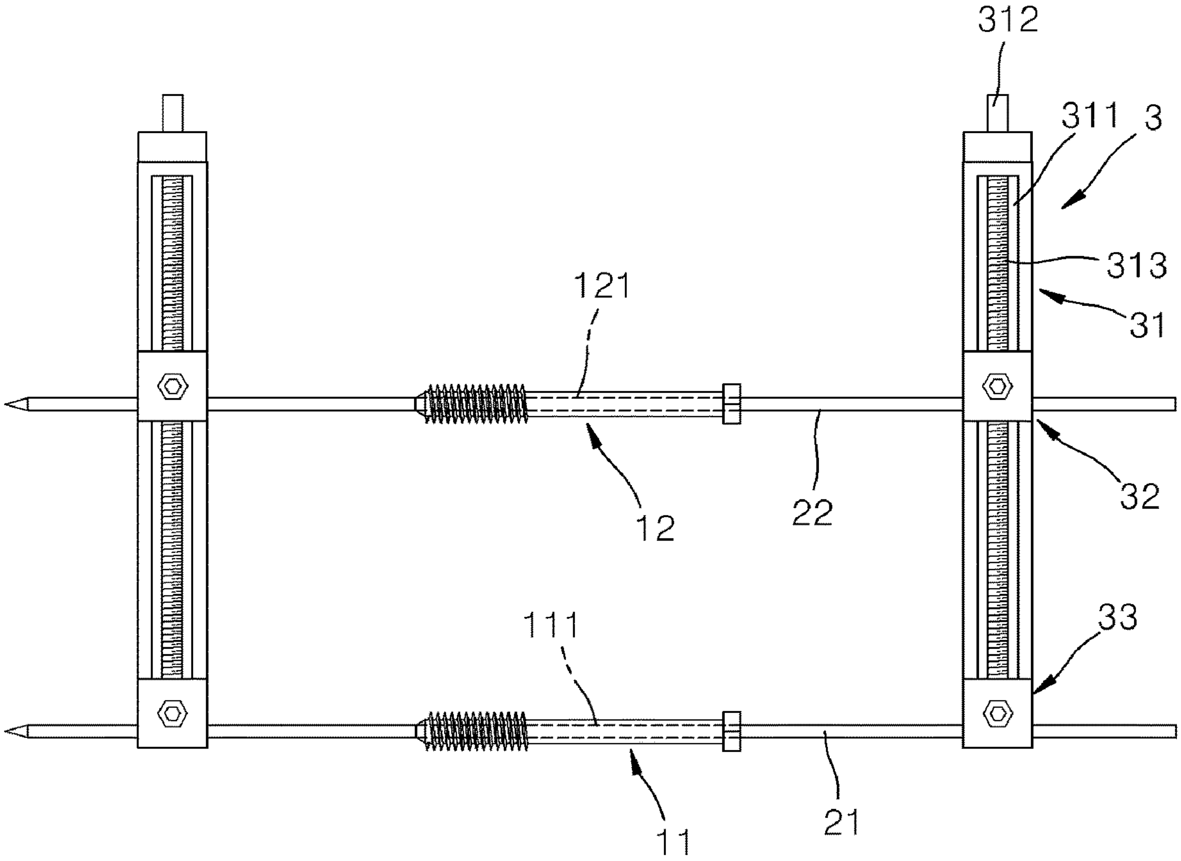
FIG. 3 is a front view of an embodiment of the present disclosure.
Figure 4:
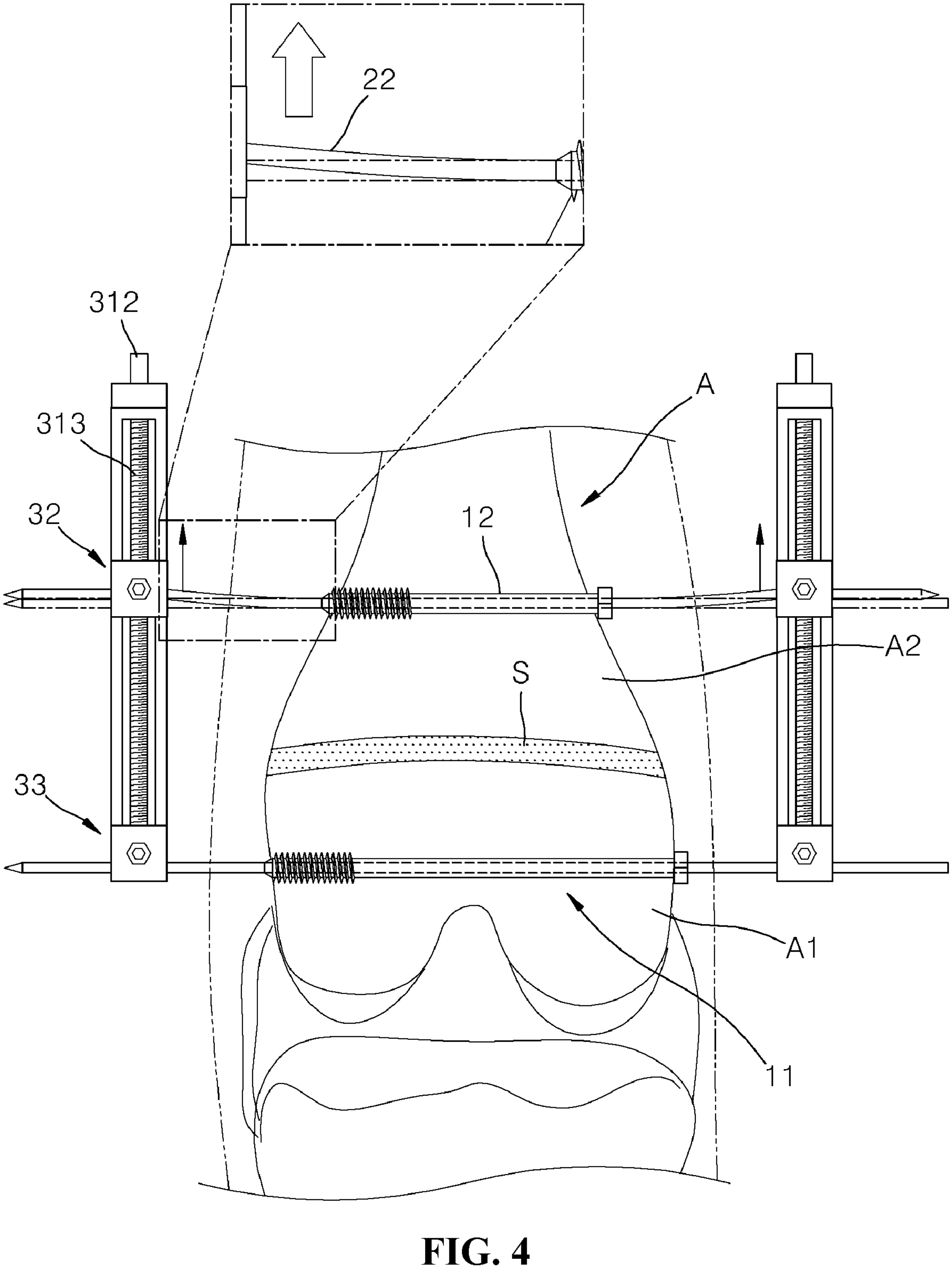
FIG. 4 is a use state view of an embodiment of the present disclosure.

FIG. 1 is a perspective view of a bone growth stimulator according to an embodiment of the present invention. FIG. 2 is an exploded perspective view of an embodiment of the present invention. FIG. 3 is a front elevation view of an embodiment of the present invention. FIG. 4 is a use state view of an embodiment of the present invention.

As shown in FIGS. 1 through 4, the bone growth stimulator according to an embodiment of the present invention is provided to promote growth of a long bone A by applying a tensile force to a growth plate S existing between a metaphysis portion A1 and an epiphysis portion A2 constituting the long bone A, and includes a first screw 11, a second screw 12, a first rod pin 21, and a second rod pin 22.

The first screw 11 is fastened to the metaphysis portion A1 located on an upper side of the growth plate S, and a channel 111 penetrating between a front end and a rear end is formed on the first screw 11. In the present embodiment, the first screw 11 is configured to be fastened to the metaphysis portion A1. However, the present invention is not limited thereto, and the first screw 11 may be attached to the other portions of the long bone A to promote bone growth.

The second screw 12 is fastened to the epiphysis portion A2 located on a lower side with the growth plate S while being disposed in parallel to the first screw 11, and a channel 121 penetrating between a front end and a rear end is formed on the second screw 12.

The first rod pin 21 is formed to extend along a unidirectional axis with a less thickness than the first screw 11, and has one side penetrating a human tissue surrounding the long bone A and being inserted into the channel 111 of the first screw 11 and the other side being exposed to the outside of the human tissue.

Similar to the first rod pin 21, the second rod pin 21 is formed to extend along a unidirectional axis with a less thickness than the second screw 12, and has one side penetrating a human tissue surrounding the long bone A and being inserted into the channel 121 of the second screw 12 and the other side being exposed to the outside of the human tissue.

A pressing unit 3 applies a force in a direction that causes the first rod pin 21 to be apart from the second rod pin 22. For example, the pressing unit 3 may be implemented by various configurations, such as an embodiment in which a spring is disposed between the first rod pin 21 and the second rod pin 22 to space the first rod pin 21 apart from the second rod pin 22 by an elastic force of the spring.

The bone growth stimulator according to an embodiment of the present invention having such a configuration as described above implants the first screw 11 and the second screw 12 in the long bone A with the growth plate S interposed therebetween, inserts the first and second rod pins 21 and 22, which are thinner and longer than the first and second screws 11 and 12, into the channels 111 and 121 of the first and second screws 11 and 12 so that respective both ends of the first and second rod pins 21 and 22 are exposed to the outside, and applies a force to the exposed both ends by using the pressing unit 3 such that the first rod pin 21 is spaced apart from the second rod pin 22, so that, even when a force greater than an optimum value required to elongate the growth plate S is applied to the second rod pin 22, the applied force gradually decreases from the exposed end of the second rod pin 22 to a portion of the second rod pin 22 in contact with the second screw 12 implanted in the bone due to the bending characteristics of the second rod pin 22 formed to be thinner and longer than the second screw 12 and the characteristics that the second rod pin 22 restores to its original shape after being bent, as well shown in a magnified portion of FIG. 4. Thus, a large force is prevented from being suddenly transmitted to the bone through the second screw 12, and consequently, damage or breakage of the bone during a procedure for elongating the growth plate S may be suppressed, and growth of the growth plate S may be promoted.

The pressing unit 3 employed in the present embodiment includes a pair of guide bodies 31 disposed outside the skin with the long bone A interposed therebetween, a fixing member 33 fixed to one end of each of the guide bodies 31, and a movable member 32 movably installed on each of the guide bodies 31.

In each of the guide bodies 31, a guide groove 311 for guiding a movement of the movable member 32 is formed on an inner side, a transfer screw (313) is rotatably installed in the guide groove 311, and a rotation knob 312 dynamically connected to the transfer screw is rotatably installed on an outer side.

The movable member 32 includes a nut portion 321, a seating portion 322, and a pressing portion 323. The nut portion 321 is inserted into the guide groove 311 and is screw-coupled to the transfer screw, the seating portion 322 is integrally formed with the nut portion 321, is exposed to the outside of the guide groove 311, and has a seating groove 322*a* on which the second rod pin 22 is seated, and the pressing portion 323 has a pressing groove having a shape corresponding to the seating groove 322*a* of the seating portion 322 and serves to selectively fix the second rod pin 22 placed on the seating portion 322 according to the degree of fastening of a fastening screw 324 to the seating portion 322.

The fixing member 33 includes a seating portion 332 and a pressing portion 333, similar to the movable member 32, but, unlike the movable member 32, does not include a nut portion. The seating portion 322, on which the first rod pin 21 is mounted is fixed to an end of each of the guide bodies 31.

In the present embodiment having such a configuration, when an operator rotates the rotation knob 312 of the pressing unit 3 to rotate the transfer screw of the guide body 31, the movable member 32 on which the second rod pin 22 is mounted is moved in a direction away from the first rod pin 21 along the guide groove 311 of the guide body 31 to exert an upward force on the second screw 12 implanted on the upper sided of the growth plate S. Thus, an instrument for promoting bone growth may be easily and conveniently handled.

A bone growth stimulator according to another embodiment of the present invention will now be described in detail with reference to FIG. 5.

Figure 5:
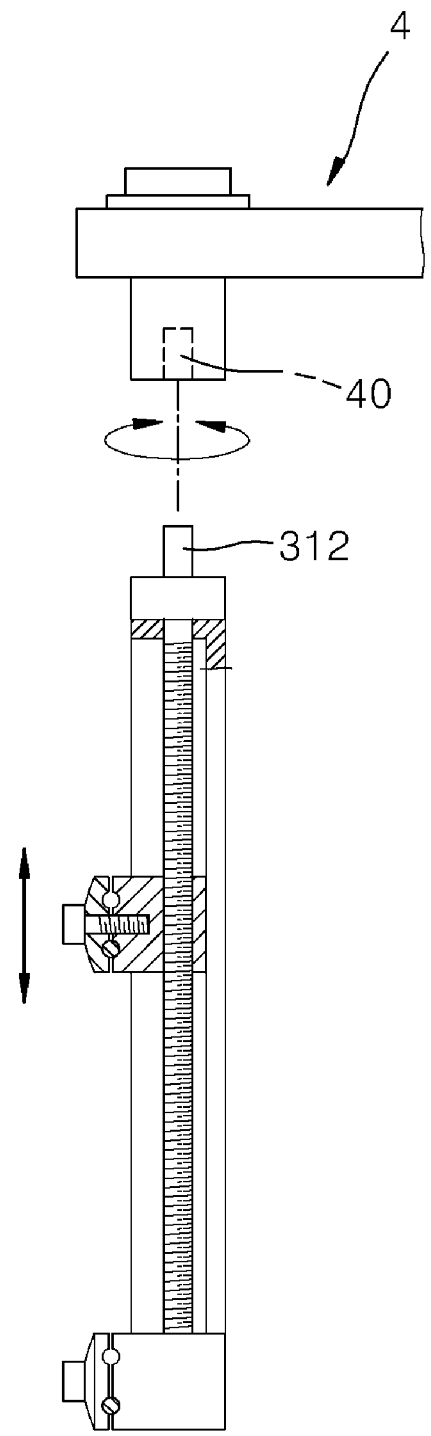
FIG. 5 is a cross-sectional side view of a portion of a bone growth stimulator according to another embodiment of the disclosure.

FIG. 5 is a cross-sectional side view of a portion of a bone growth stimulator according to another embodiment of the present invention.

The present embodiment further includes a torque wrench 4 connected to the rotation knob 312 rotatably installed on a guide body, in addition to the configuration of the previous embodiment.

The torque wrench 4 includes a connection groove 40 for connection with the rotation knob 312 and is rotated by the operator's handling while being connected to the rotation knob 312 through the connection groove 40. In a case where a torque of a certain magnitude or more is applied during this manipulation process, a well-known mechanism prevents the torque from being applied to the rotation knob 312, so that an excessively large force may be prevented from being transmitted to bones through a rod pin and a screw due to the operator's carelessness.

Figure 6:
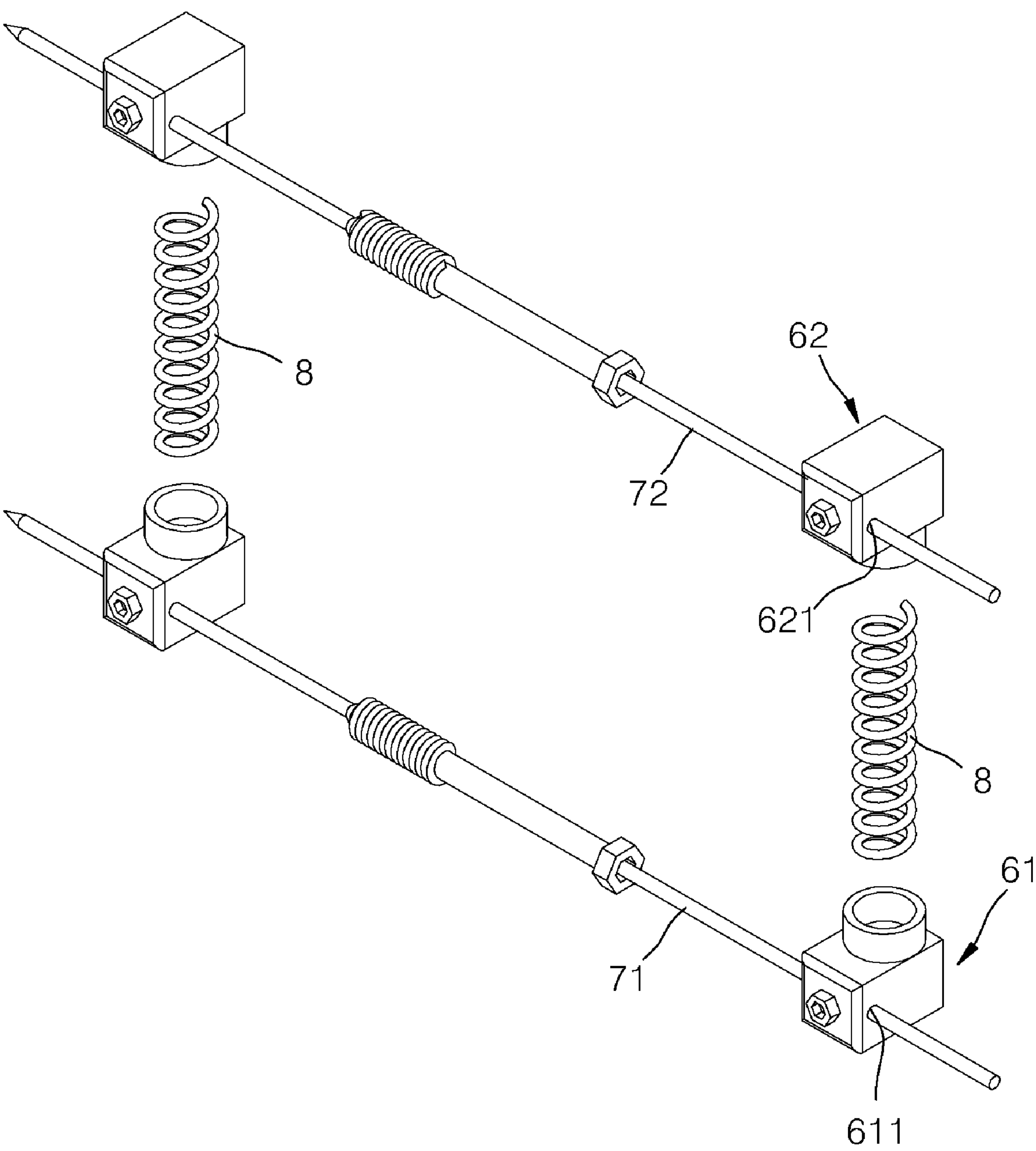
FIG. 6 is an exploded perspective view of a bone growth stimulator according to another embodiment of the present disclosure.
Figure 7:
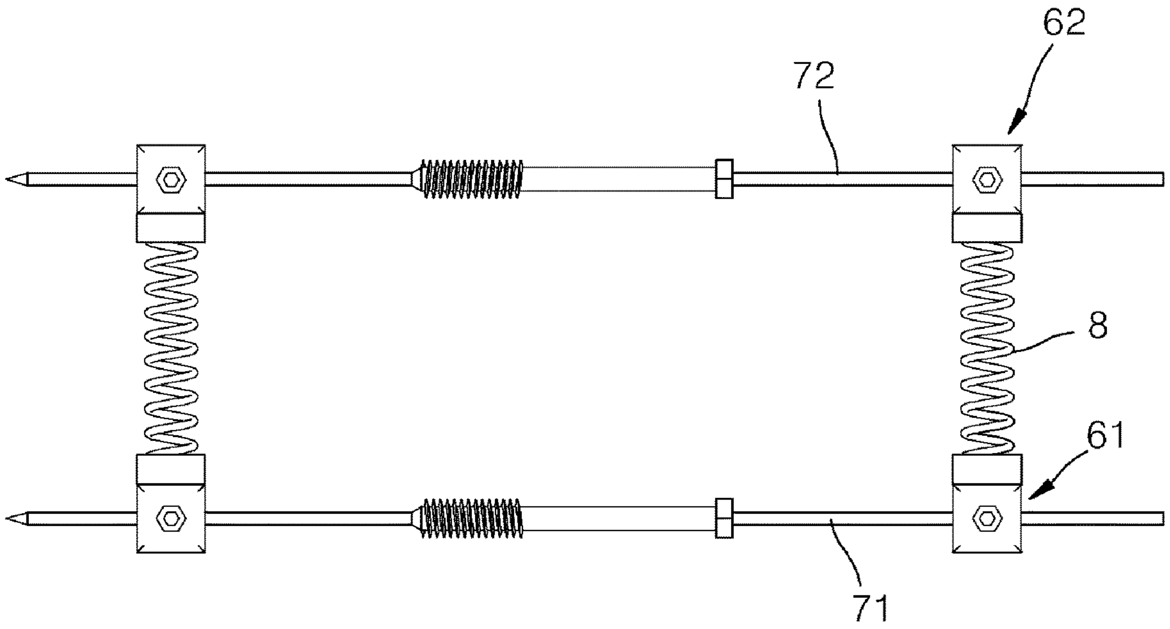
FIG. 7 is a front view showing another embodiment of the present disclosure in a coupled state.

FIG. 6 is an exploded perspective view of a bone growth stimulator according to another embodiment of the present invention, and FIG. 7 is a front view showing another embodiment of the present invention in a coupled state.

A pressing unit employed in the present embodiment includes a first connection member 61, a second connection member 62, and an elastic member 8.

The first connection member 61 has a through hole 611 through which the first rod pin 71 passes, and is thus connected to the first rod pin 71 through the through hole 611*m* and the second connection member 62 has a through hole 621 through which the second rod pin 72 passes, and is thus connected to the second rod pin 72 through the through hole 621.

The elastic member 8 is interposed between the first connection member 61 and the second connection member 62 and applies a force in a direction for spacing the second connection member 62 away from the first connection member 61.

The present embodiment having such a configuration is configured such that a spring having an elastic force corresponding to a required pressurizing force is interposed between the first connection member 61 and the second connection member 62 in a customized way, so that sudden application of a large force to bones may be prevented and a patient-specific procedure may be performed.

Figure 8:
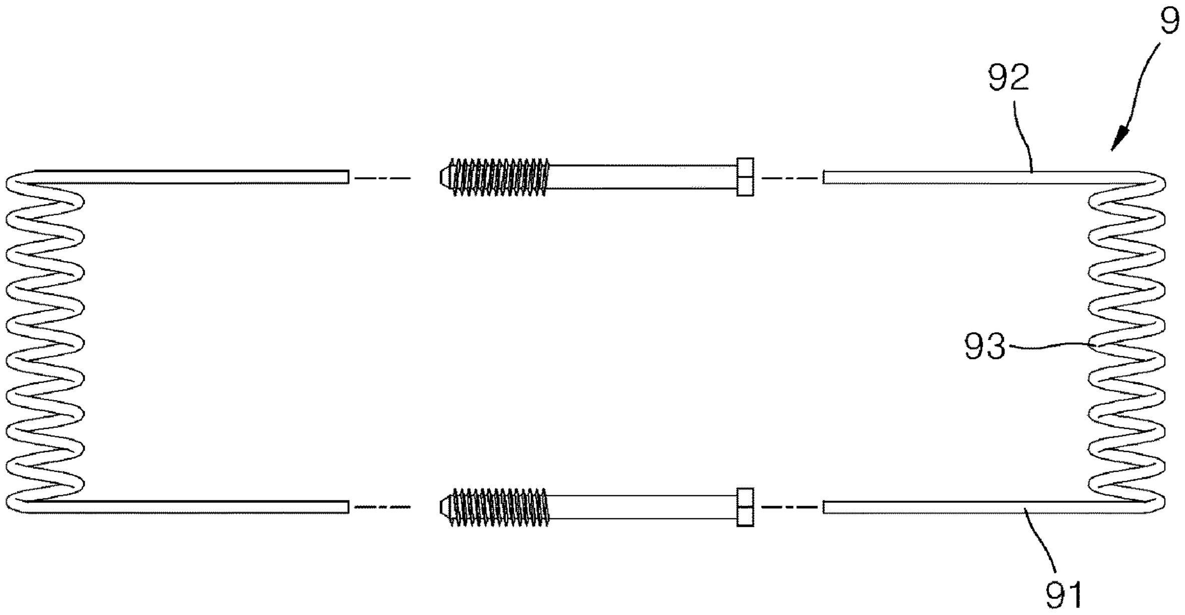
FIG. 8 is an exploded front view of a structure according to another embodiment of the present disclosure.

FIG. 8 is an exploded front view of a structure according to another embodiment of the present invention.

A pressing unit 9 employed in the present embodiment includes an elastic member 93 interposed between the first rod pin 91 and the second rod pin 92 in a coiled shape to apply an elastic force to the first rod pin 91 and the second rod pin 92. It is preferable that the elastic member 93 is integrally formed with the first rod pin 91 and the second rod pin 92 so that medical expenses may be reduced through a simplified configuration and convenience of an operation may be increased.

In the present embodiment having such a configuration, when an operator inserts each of the first and second rod pins 91 and 92 into a screw in a state in which the elastic member 93 is compressed using a novel mechanism, an elastic force held by the compression is applied to the screw through each of the first and second rod pins 91 and 92, so that bone growth may be promoted.

Although various embodiments of the present invention have been described above, the present embodiment and the drawings attached to this specification only clearly show a portion of the technical idea included in the present invention, and it will be apparent that all modifications and specific embodiments that can be easily inferred by those skilled in the art within the scope of the technical spirit included in the drawings included in the specification and drawings of the present invention are included in the scope of the present invention.

DESCRIPTION OF REFERENCE NUMERALS

| | |
|---|---|
| 11: first screw | 111: channel |
| 12: second screw | 121: channel |
| 21: first rod pin | 22: second rod pin |
| 3: pressing unit | 31: guide body |
| 311: guide groove | 312: rotation knob |
| 32: movable member | 321: nut portion |
| 322: seating portion | 322a: seating groove |
| 323: pressing unit | 324: fastening screw |
| 33: fixing member | 332: seating portion |
| 333: pressing unit | A: long bone |
| A1: metaphysis portion | A2: epiphysis portion |
| S: growth plate | |

The invention claimed is:

1. A bone growth stimulator comprising:

a first screw configured to be fastened to a metaphysis portion and having a first channel penetrating between a first front end and a first rear end;

a second screw configured to be fastened to an epiphysis portion and disposed in parallel to the first screw, the second screw having a second channel penetrating between a second front end and a second rear end;

a first rod pin having a first side configured to pass through tissue that surrounds a bone and to be inserted into the first channel of the first screw, and a first another side configured to be exposed to an outside of the tissue;

a second rod pin having a second side configured to pass through tissue that surrounds the bone and to be inserted into the second channel of the second screw, and a second another side configured to be exposed to the outside of the tissue; and a pressing assembly having a configuration to move the second rod pin in a direction to space the second rod pin apart from the first rod pin, the pressing assembly comprising:

a pair of guide bodies, wherein each of the pair of guide bodies includes:

a guide groove defining an inner space thereof, a transfer screw configured to rotate and installed within the guide groove, and a rotation knob connected to the transfer screw and configured to rotate installed on a first end of each of the pair of guide bodies, a fixing member fixed to each of the pair of guide bodies and on which the first rod pin is selectively mounted, and a movable member installed on each of the pair of guide bodies and including a nut portion screw-coupled to the transfer screw and a seating portion on which the second rod pin is selectively mounted, wherein the pair of guide bodies include a first guide body and a second guide body respectively disposed on opposite sides of the bone with the bone interposed therebetween, the first guide body and the second guide body extending parallel to each other, wherein the nut portion and the seating portion of the movable member are integrally formed, and wherein the movable member includes a seating groove defined directly on the seating portion and configured to receive the second rod pin thereon.

2. The bone growth stimulator of claim 1, further comprising a torque wrench connected to the rotation knob to apply a torque of less than a set value to the rotation knob.

3. The bone growth stimulator of claim 1, wherein an inner diameter of the first channel is substantially equal to an outer diameter of the first rod pin.

4. The bone growth stimulator of claim 1, wherein an inner diameter of the second channel is substantially equal to an outer diameter of the second rod pin.

5. The bone growth stimulator of claim 1, wherein the first screw includes a first helical thread on the first front end.

6. The bone growth stimulator of claim 1, wherein the second screw includes a second helical thread on the second front end.

7. The bone growth stimulator of claim 1, wherein a first expanded end is defined at the first rear end of the first screw, where an outer diameter of the first expanded end is larger than an outer diameter of the first channel.

8. The bone growth stimulator of claim 1, wherein a second expanded end is defined at the second rear end of the second screw, where an outer diameter of the second expanded end is larger than an outer diameter of the second channel.

9. The bone growth stimulator of claim 1, wherein the seating portion of the movable member is exposed outside the guide groove of each of the pair of guide bodies, while the nut portion is entirely disposed within the guide groove.

10. The bone growth stimulator of claim 1, wherein the rotation knob protrudingly extends outward from an outer side of the first end of each of the pair of guide bodies.

11. A method of stimulating bone growth, the method comprising:

fastening a first screw to a metaphysis portion, the first screw having a first channel penetrating between a first front end and a first rear end;

fastening a second screw to an epiphysis portion, the second screw being disposed in parallel to the first screw and having a second channel penetrating between a second front end and a second rear end;

inserting a first side of a first rod pin through tissue that surrounds a bone into the first channel of the first screw, with a first another side of the first rod pin exposed to an outside of the tissue;

inserting a second side of a second rod pin through tissue that surrounds the bone into the second channel of the second screw, with a second another side of the second rod pin exposed to the outside of the tissue; and moving the second rod pin in a direction to space the second rod pin apart from the first rod pin using a pressing assembly, the pressing assembly comprising:

a pair of guide bodies, wherein each of the pair of guide bodies includes:

a guide groove defining an inner space thereof, a transfer screw configured to rotate and installed within the guide groove and a rotation knob connected to the transfer screw and configured to rotate installed on a first end of each of the pair of guide bodies, a fixing member fixed to each of the pair of guide bodies at a second end opposite the first end of each of the pair of guide bodies and on which the first rod pin is selectively mounted, and a movable member installed on each of the pair of guide bodies and including a nut portion screw-coupled to the transfer screw and a seating portion on which the second rod pin is selectively mounted, wherein the pair of guide bodies include a first guide body and a second guide body respectively disposed on opposite sides of the bone with the bone interposed therebetween, the first guide body and the second guide body extending parallel to each other, wherein the nut portion and the seating portion of the movable member are integrally formed, and wherein the movable member includes a seating groove defined directly on the seating portion and configured to receive the second rod pin thereon.

12. The method of claim 11, further comprising applying a torque of less than a set value to the rotation knob using a torque wrench connected to the rotation knob.

13. The method of claim 11, wherein an inner diameter of the first channel is substantially equal to an outer diameter of the first rod pin.

14. The method of claim 11, wherein an inner diameter of the second channel is substantially equal to an outer diameter of the second rod pin.

15. The method of claim 11, wherein the first screw includes a first helical thread on the first front end.

16. The method of claim 11, wherein the second screw includes a second helical thread on the second front end.

17. The method of claim 11, wherein a first expanded end is defined at the first rear end of the first screw, where an outer diameter of the first expanded end is larger than an outer diameter of the first channel.

18. The method of claim 11, wherein a second expanded end is defined at the second rear end of the second screw, where an outer diameter of the second expanded end is larger than an outer diameter of the second channel.

* * * * *